United States Patent

Umeda

[11] Patent Number: 5,952,554
[45] Date of Patent: Sep. 14, 1999

[54] METHOD FOR TESTING FREQUENCY RESPONSE CHARACTERISTICS OF LASER DISPLACEMENT/VIBRATION METERS

[75] Inventor: Akira Umeda, Tsukuba, Japan

[73] Assignee: Director-General of the Agency of Industrial Science and Technology, Tokyo, Japan

[21] Appl. No.: 08/698,460

[22] Filed: Aug. 15, 1996

[30] Foreign Application Priority Data

Aug. 18, 1995 [JP] Japan ..................... 7-210704

[51] Int. Cl.⁶ ............. G01B 21/00; G01B 9/02; G01N 29/00
[52] U.S. Cl. ............. 73/1.79; 73/1.86; 73/1.82; 356/345; 356/358
[58] Field of Search ................... 73/1 DV, 1 D, 73/657, 1.86, 1.37–1.41, 1.79, 1.81, 1.82; 356/345, 358, 356, 243

[56] References Cited

U.S. PATENT DOCUMENTS

| | | | |
|---|---|---|---|
| 3,693,400 | 9/1972 | Savit | 73/1.85 |
| 4,355,900 | 10/1982 | Nussmeir | 356/356 |
| 4,659,224 | 4/1987 | Monchalin | 73/657 |
| 5,000,030 | 3/1991 | Umeda et al. | |
| 5,039,221 | 8/1991 | Layton et al. | 356/345 |
| 5,353,642 | 10/1994 | Hasegawa et al. | 73/1.38 |

OTHER PUBLICATIONS

Bouch et al., "Calibrators for Acceptance and qualification Testing of Vibration Measuring Instruments," pp. 1–13, Dec. 1963.

Clark, "An Improved Method for Calibrating Reference Standard Accelerometers", 1970 pp. 103–107.

*Primary Examiner*—Hezron Williams
*Assistant Examiner*—Chad Soliz
*Attorney, Agent, or Firm*—Oblon, Spivak, McClelland, Maier & Neustadt, P.C.

[57] ABSTRACT

A method of testing frequency characteristics of a laser displacement/vibration meter by the use of a novel method which can cope with a broader frequency range and finer micro-level displacements to enhance the reliability of the displacement/vibration meter. Upon applying impact on one end face of a round metal rod, an elastic wave pulse which propagates through the metal rod generates a stepwise dynamic displacement of the other end face of the rod when reflected there. This dynamic displacement is measured simultaneously by a reference laser interferometer with a reference laser beam and a laser displacement/vibration meter with unknown frequency response characteristics, followed by comparison of measurement data over a frequency range to determine the frequency response characteristics of the unknown laser displacement/vibration meter.

3 Claims, 4 Drawing Sheets

METHOD FOR TESTING FREQUENCY RESPONSE CHARACTERISTICS OF LASER DISPLACEMENT/VIBRATION METERS

BACKGROUND OF THE INVENTION

1. Field of the Art

This invention relates to a method for testing frequency characteristics of laser displacement/vibration meters which are widely in use in industrial fields. A laser displacement/vibration is an instrument used to measure a displacement or a vibration of an object's surface using laser illumination and a process of reflected light. More particularly, this invention concerns a method for testing frequency characteristics of a laser displacement/vibration meter for the purpose of establishing traceability in the measurement of high-speed micro-level displacements and micro-level vibrations, by comparing measurement data of a laser displacement/vibration meter and a reference laser interferometer with a reference laser bean or a laser interferometer of a similar class, employing a novel technology for generating high-speed micro-level fine displacements or vibrations.

2. Prior Art

Laser displacement/vibration meters have thus far been in wide use in industrial fields for measurement of displacements and vibrations according to the principles of light-wave interference based on Doppler shifts and heterodyne light-wave interference. However, it has been infeasible to assess the reliability and accuracy of laser displacement/vibration meters of this nature due to absence of technology of generating high-speed micro-level fine displacements over a wide frequency range where the frequency is close to a DC component.

On the other hand, as evidenced by the developments in the so-called micromachine technology in advanced western countries, there have been increasing necessities for measuring movements of microstructures far smaller than conventional counterparts, over a frequency range broader than was necessary heretofore. It follows that severe requirements are imposed on a laser displacement/vibration meter especially on the reliability and accuracy of measurement. As a consequence, users and manufacturers of meters of this sort are in need of a new method for generating high-speed micro-level displacements or high-speed micro-level vibrations which are difficult to generate with conventional methods.

SUMMARY OF THE INVENTION

In view of the foregoing circumstances, it in an object of the present invention to provide a method for testing frequency response characteristics of a laser displacement/vibration meter, which can cope with a broader frequency range and displacements of a finer level to ensure higher reliability in the measurement of micro-level fine displacements and vibrations.

It is a more specific object of the present invention to establish reliable traceability in the measurement of high-speed micro-level fine displacements and vibrations by determining a measurable frequency range of a laser displacement/vibration meter, not from a theoretical analogy based on the principles of Doppler shifts or the like but from comparison of actual measurement data of a reference laser interferometer using a reference laser beam or a laser interferometer of a similar class and of a laser displacement/vibration meter with unknown frequency response characteristics.

In accordance with the present invention, for achieving the above-stated objectives, there is provided a method for testing frequency response characteristics of a laser displacement/vibration meter, which essentially comprises the steps of: applying impact on one end face of a round metal rod to produce an elastic wave pulse propagating toward the other end of the rod to generate stepwise dynamic displacement of the other end face of the rod by reflection of the elastic wave pulse; measuring the dynamic displacement of the other end face of the rod simultaneously by a reference laser interferometer with a reference laser beam and a laser displacement/vibration meter with unknown frequency characteristics; and determining frequency response characteristics of the unknown laser displacement/vibration meter by comparison of measurement data with the counterpart data of the reference laser interferometer. Stepwise dynamic displacement refers to a displacement which is generated when an elastic wave pulse propagates through a body of a rod and rebounds at an end face.

In the practice of the testing method just described, there may arise a situation where it is difficult to use a reference laser interferometer in an actual spot of measurement. In such a case, namely, in case a reference laser interferometer is not available in an actual spot of measurement, the performance of a laser displacement/vibration meter with unknown frequency response characteristics is assessed preliminarily on the basis of measurement data obtained from a strain gage which is bonded on a lateral side of the round metal rod, and determining the frequency response characteristics of the laser displacement/vibration meter afterwards by application of a corrective function, which is determined by measurement with a reference laser interferometer. As a reuslt, the frequency characteristics of the laser displacement/vibration meter can be assessed as accurately as in the measurement using a reference laser interferometer simultaneously in a measuring spot.

In accordance with the present invention, there is also provided a method for testing frequency response characteristics of a laser displacement/vibration meter, suitable for use in the measurement of dynamic displacements in a frequency range higher than several hundreds kHz, the method comprising the steps of: applying an impulse voltage to a piezoelectric vibrator in the form of a piezoelectric element or a piezoelectric film to generate stepwise dynamic displacement on the surface of the piezoelectric vibrator; measuring the dynamic displacements of the piezoelectric vibrator surface simultaneously by a reference laser interferometer with a reference laser beam and a laser displacement/vibration meter with unknown frequency response characteristics; and determining frequency response characteristics of the unknown laser displacement/vibration meter by comparison of measurement data with counterpart data of the reference laser interferometer over a frequency range.

Further, according to the present invention, there is further provided a method for testing frequency response characteristics of a laser displacement/vibration meter, particularly suitable for use in a measurement of dynamic displacements in a frequency range higher than several hundreds kHz and for use in a case where an impulsive displacement or amplitude of vibration resulting from application of an impulse voltage to a piezoelectric vibrator is smaller than laser bean wavelength, the method comprising the steps of: providing a piezoelectric film on an end face of a stack of piezoelectric elements; applying an impulse voltage to the stack of piezoelectric elements to generate micro-level fine displacements on a surface of the piezoelectric film; measuring the fine displacements of the piezoelectric film surface by a reference laser interferometer with a reference laser beam to determine a phase correction value according to resulting measurement data; measuring high-speed micro-level fine displacements of the piezoelectric film surface simultaneously by the use of the reference laser interferometer and a laser displacement/vibration meter with unknown frequency response characteristics; and determining frequency response characteristics of the displacement/vibration meter by comparison of measurement data with the counterpart data of the reference laser interferometer as corrected with the correction value.

The above and other objects, features and advantages of the invention will become apparent from the following particular description of the invention, taken in conjunction with the accompanying drawings which show by way of example preferred embodiments of the invention.

DESCRIPTION OF PREFERRED EMBODIMENTS

Now, the invention is described more particularly by way of its preferred embodiments with reference to the drawings.

Figure 1:
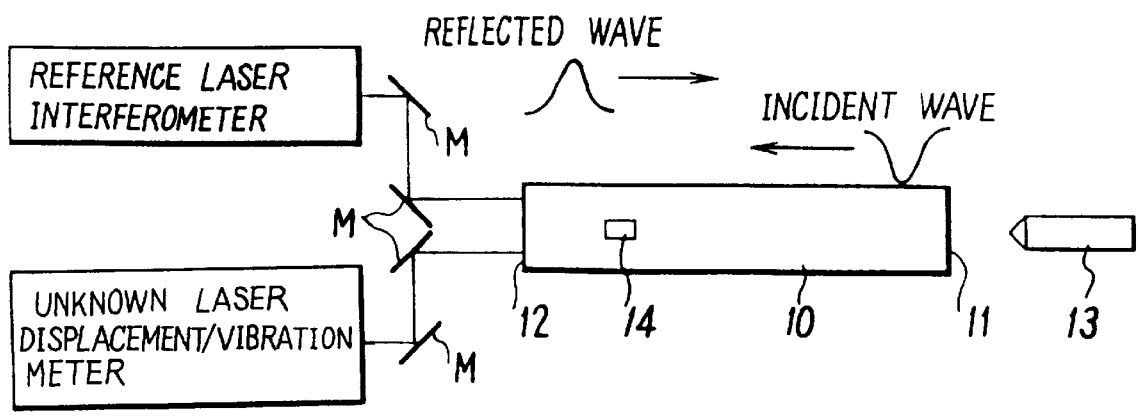
FIG. 1 is a block diagram explanatory of a first embodiment of the invention.
Figure 2A:
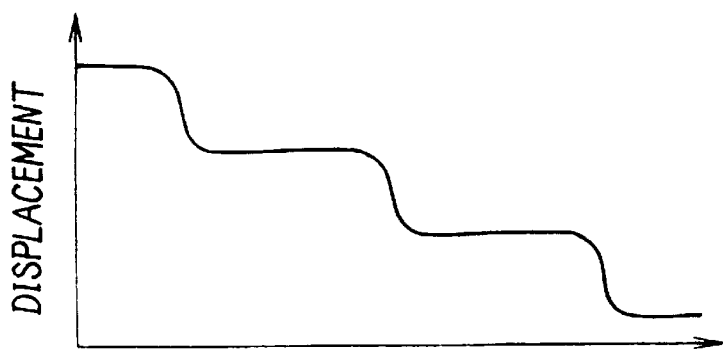
FIG. 2 shows graphs (a) and (b) plotting movements of an end face of a round rod in FIG. 1.
Figure 2B:
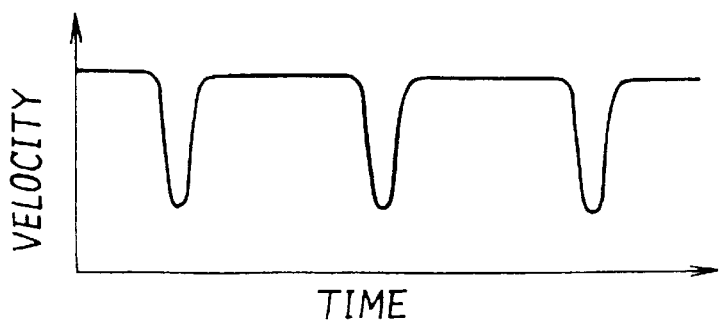

Shown in FIGS. 1 and 2 is a first embodiment of the present invention, i.e., a method for testing frequency characteristics of a laser displacement/vibration meter.

In order to clarify the performance quality of a displacement meter or of a vibration meter with unknown frequency characteristics, it is necessary to test it by comparing its measurement data with counter measurement data produced by a reference displacement meter or vibration meter. In this connection, what is imperative to the test is how to put a surface in micro-level fine vibrational movements over a wide frequency range.

To create a vibrating surface of such nature, a round metal rod 10, which has a relatively large length as compound with it diameter as shown in FIG. 1, is employed in this particular embodiment. More specifically, for this purpose, impact is applied to one end face 11 of the round rod 10 by colliding thereagainst a flying body 13, sending forth an elastic wave pulse through the rod 10 to generate stepwise dynamic displacement of the other and face 12 of the rod 10. Although not shown in the drawings, the round rod 10 is supported on two rows of bearing balls which are placed in V-grooves to hold the rod 10 in an unrestricted state in the axial direction thereof.

More particularly, the elastic wave pulse, which is generated in the rod 10 upon hitting the flying body 13 against one end face 11 of the rod 10, propagates through the body of the rod 10 as a compressive elastic wave pulse. Upon reaching the other end face 12 of the rod 10, the elastic wave pulse is reflected to return as a tensile elastic wave pulse. At the tine of reflection, the elastic wave pulse generates impulsive dynamic displacement of the end face 12 in the vertical direction. FIG. 2 illustrates the movements which occur to the end face 12 of the rod 10, i.e., its displacements in graph (a) and its velocity in graph (b). Uniform movement of the end face 12 of the rod 10 is ensured in case the length of the rod 10 is more then 15 times as large as its diameter. The frequency range of the induced dynamic displacements normally extends from almost a DC component to several hundreds kHz, and can be set to a desired frequency coverage through selection of suitable factors in material properties, diameter and length of the round rod.

According to the invention, in order to permit a reference laser interferometer with a reference laser beam and a laser displacement/vibration meter with unknown frequency characteristics to make measurements of dynamic displacements simultaneously in the same plane, the flying body 12 is driven to hit against the end face 11 of the rod 10 while simultaneously projecting thereon the beams of the reference laser interferometer and the unknown laser displacement/vibration meter, if necessary, by the use of a mirror M. As a consequence, it becomes possible to test the frequency characteristics of the unknown laser displacement/vibration meter by comparison of its measurement data with the corresponding measurement data of the reference laser interferometer.

More specifically, with a reference laser interferometer having a reference laser beam for measuring the velocity of a moving surface (i.e., the end face 12 of the round rod 10), frequency characteristics $G_d(j\omega)$ of an unknown laser displacement meter can be determined according to Equation (1) below.

$$G_d(j\omega) = \frac{j\omega L[d_u(t)]}{L[v_d(t)]} \quad (1)$$

where L is Laplace transformation operator, ω is the angular frequency, $d_u(t)$ is the displacement output of the unknown laser displacement meter, $v_d(t)$ is the velocity measured by the reference loser interferometer, and t is time.

On the other hand, frequency characteristics $G_v(j\omega)$ of an unknown laser vibrometer can be determined according to Equation (2) below.

$$G_v(j\omega) = \frac{L[v_u(t)]}{L[v_d(t)]} \quad (2)$$

where $v_u(t)$ in the velocity output of the unknown laser vibrometer.

In case a reference laser interferometer with a reference laser beam is unavailable on an actual measuring spot, the frequency characteristics of a laser displacement/vibration meter can be tested with similarly high accuracy by means of a strain gage 14 which is bonded on a lateral side of the round metal rod 10 as shown in FIG. 1, using in place of the measurement data of a reference laser interferometer measurement data of the strain gage 14 based on its signals and corrected by a corrective function for the testing frequency range, in determining the frequency characteristics of the laser displacement/vibration meter.

More specifically, in this case, subsequent to assessment of characteristics of a laser displacement or vibration meter with unknown frequency response characteristics, corrections are made to the measurement data with regard to the dispersion of the elastic wave in the course of its propagation, using a corrective function determined by a measurement with a reference laser interferometer having a reference laser beam. Accordingly, even if a reference laser interferometer is not available on a measuring spot, it is possible to assess the frequency characteristics with the same high accuracy as the assessment made directly by the use of a reference laser interferometer.

In this instance, according to the one-dimensional wave motion theory, if the output of the strain gage 14 bonded on a lateral side of the round rod 10 is $\epsilon E_m$, the displacement $d_e$, velocity $v_e$ and acceleration $a_e$ of the round rod 10 are $$d_e 2C \int \epsilon_m(t) dt \qquad (3)$$

$$v_e = 2C \epsilon_m(t) \qquad (4)$$

$$a_e = 2C \dot{\epsilon}_m(t) \qquad (5)$$

where C is the propagation velocity of longitudinal elastic wave through the round rod 10.

In case of a laser vibrometer for measuring the velocity of vibration of an object surface, firstly the frequency characteristics $G_{vle}(j\omega)$ before corrections, of the vibrometer are determined on the basis of the one-dimensional wave motion theory, as expressed by the equation below.

$$G_{vle}(j\omega) = \frac{L[v_u(t)]}{L[2C\varepsilon_m(t - l/C)]} \qquad (6)$$

where l is the distance from the strain gage to the laser beam projecting end face.

In this case, however, the resulting measurement data need corrections because of uncertainty of dynamic characteristics of the strain gage including an amplifier, uncertainty of the velocity of longitudinal elastic wave, attenuation of the elastic wave, dispersion of the elastic wave pulse in the course of propagation, using a predetermined corrective function as defined by the equation below.

$$G_{cs}(j\omega) = \frac{2CL[\varepsilon_m(t - l/C)]}{L[V_{ule}(t)]} \qquad (7)$$

where $V_{ule}$ is the velocity measured by the laser interferometer.

Thus, the ultimate frequency characteristics are obtained by multiplying Eq. (6) by Eq. (7). Namely, in combination with the round metal rod having a strain gage bonded thereon, the data of the corrective function expressed by Eq. (7), determined beforehand by the use of a reference laser interferometer with a reference laser beam, can make practical transfer standards useful in testing laser vibrometers.

The same procedures can be applied to the measurement of displacements.

Figure 3:
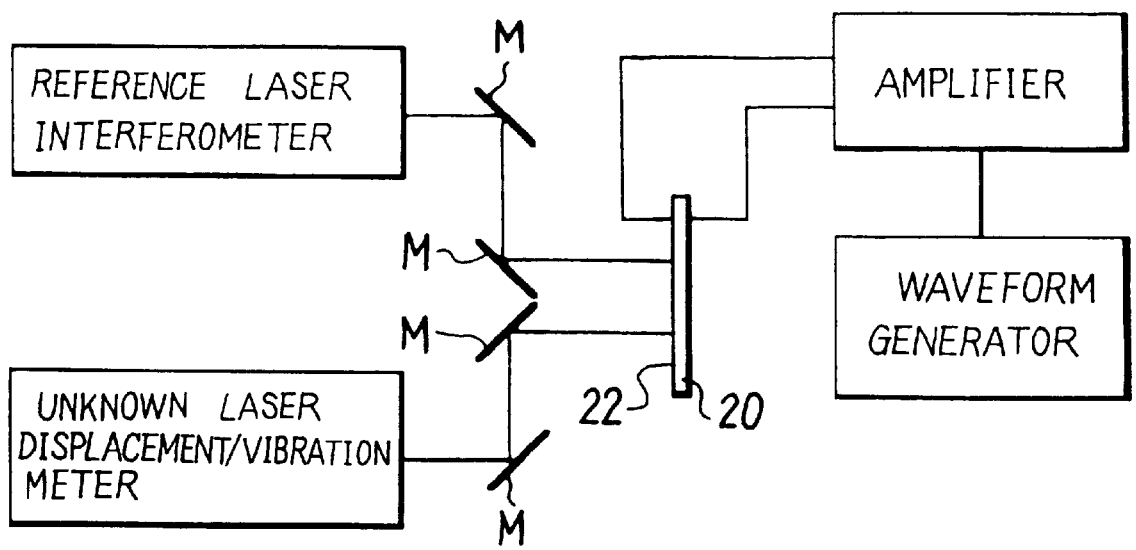
FIG. 3 is a block diagram explanatory of a second embodiment of the invention.
Figure 4:
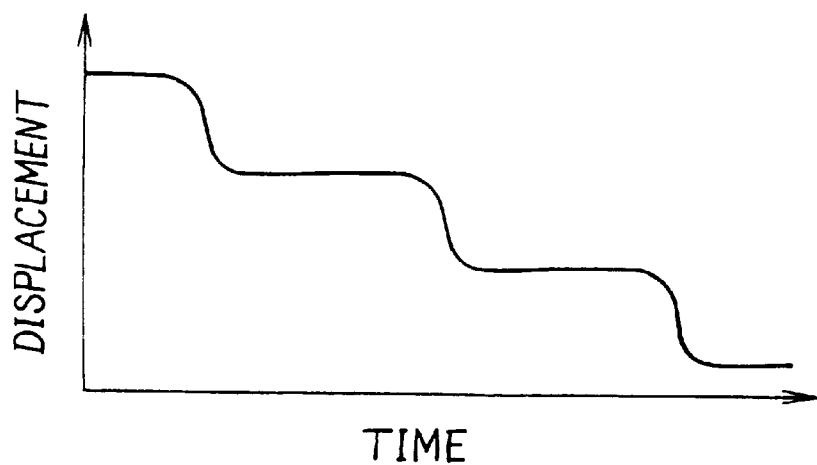
FIG. 4 in a graph plotting surface movements of a piezoelectric element in FIG. 3.

Illustrated in FIGS. 3 and 4 is a second embodiment of the present invention which it suitable for application to measurements in higher frequency ranges.

In terms of frequency range, the first embodiment of the invention, shown in FIG. 1, can cope with from a DC component up to several hundreds kHz, but not with higher frequency ranges. In order to cover a frequency range higher than several hundreds kHz or a frequency range where the impulsive displacements or the amplitude of vibration resulting from application of an impulse voltage to a piezoelectric element can be smaller than the wavelength of the laser beam, a piezoelectric vibrator 20, which is constituted by a piezoelectric element as shown in FIG. 3, is used in place of the above-described round metal rod 10, applying thereto an impulse voltage output of a waveform generator through an amplifier to generate pulse-like dynamic displacements on a measuring surface 22 of the piezoelectric element. The above-mentioned piezoelectric vibrator 20 may be constituted by a piezoelectric film if desired.

A laser beam of a reference laser interferometer and a laser beam of an unknown laser displacement/vibration meter are concurrently projected on the measuring surface 22 of the piezoelectric vibrator 20, through a mirror M if necessary, while generating stepwise dynamic displacement of the measuring surface 22. Accordingly, the dynamic displacements of the measuring surface can be measured simultaneously by the reference laser interferometer and the unknown laser displacement/vibration meter.

In this instance, however, considering the narrow frequency range of a piezoelectric vibrator, it may become necessary to employ a plural number of similar piezoelectric vibrators depending upon the dynamic range of a measuring system and the testing frequency range. The frequency characteristics of the unknown laser displacement/vibration meter are determined by the calculation as explained hereinbefore in relation with the first embodiment, which compare measurement data of the displacement/vibration meter with the counterpart data of the reference laser interferometer.

FIG. 4 graphically shows the movements which occur to the surface of the piezoelectric element.

Figure 5:
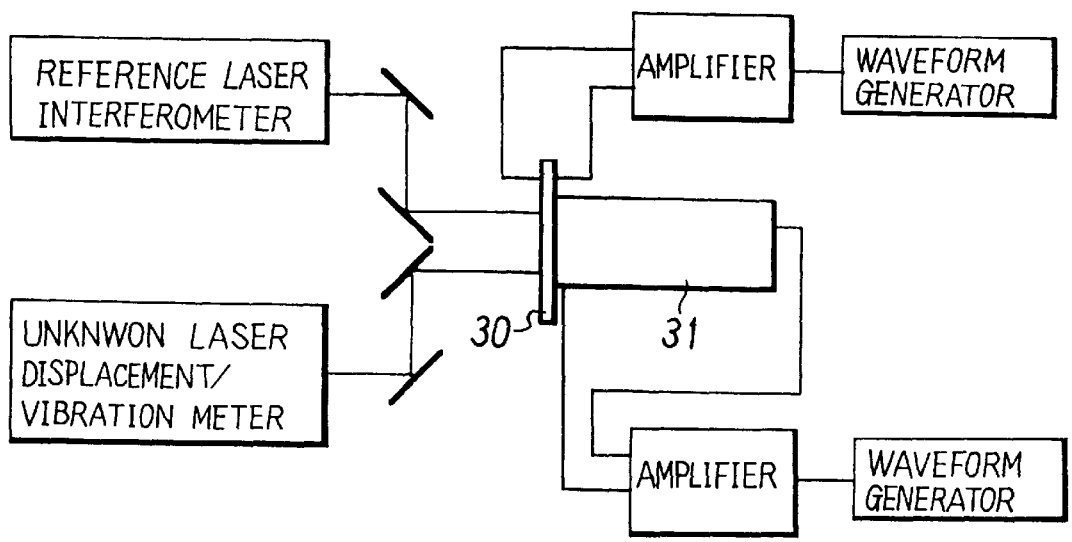
FIG. 5 is a block diagram explanatory of a third embodiment of the invention.
Figure 6:
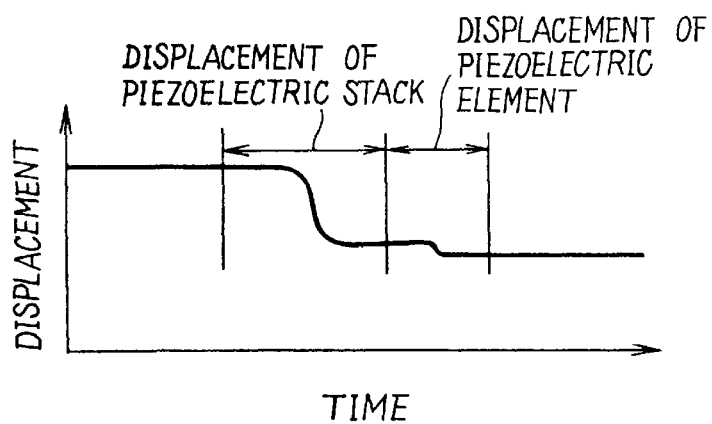
FIG. 6 is a graph plotting surface movements of a piezoelectric element in FIG. 5.

Illustrated in FIGS. 5 and 6 is a third embodiment of the invention employing a stack of piezoelectric elements.

In measuring the velocity of movements or dynamic displacements of a surface of a piezoelectric film, there may arise situations where the frequency of measurement becomes higher and at the same time the displacement or the amplitude of vibration becomes smaller than the wavelength of the laser beam. In such a case, there may be employed a piezoelectric film 30 which is set on a stack of piezoelectric elements 31 as shown in FIG. 5. In this instance, firstly pulse-like voltage is applied to the stack of piezoelectric elements to generate a dynamic displacement of the piezoelectric film surface on which the laser beams are projected, through a parallel movement of the entire piezoelectric film with the elongation of the piezoelectric stack. In this regard, since it in easy to generate displacements larger than the wavelength of the laser beam used for the laser displacement meter, interference fringes can be produced quite easily thereby to obtain correction data for reading the phases inside the fringes.

At a time point when the displacement of the piezoelectric film surface on elongation or stretching of the stack becomes to remain at a constant value, a pulse-like voltage is applied to the piezoelectric film to generate high-speed micro-level fine displacements on the piezoelectric film surface under measurement simultaneously by a reference laser interferometer with a reference laser beam and a laser displacement meter with unknown frequency characteristics. Displacement smaller than the wavelength of the laser beam can be read from the results of measurement by the reference laser interferometer after correction using the correction data obtained by the stack elongation test. Accordingly, the frequency characteristics of the unknown laser displacement meter can be clarified by comparing its measurement data with the counterpart data of the reference laser interferometer over a frequency range according to Eq. (1) given hereinbefore.

The same applies to the testing of a laser vibrometer. In case variations in light luminosity caused by variations in velocity of the piezoelectric film surface do not correspond to one fringe, phase correction data for measurement of the velocity of the piezoelectric film can be obtained by producing similar variations in velocity through elongation of the piezoelectric stack.

FIG. 6 graphically shows the movements of the piezoelectric element surface.

Figure 7:
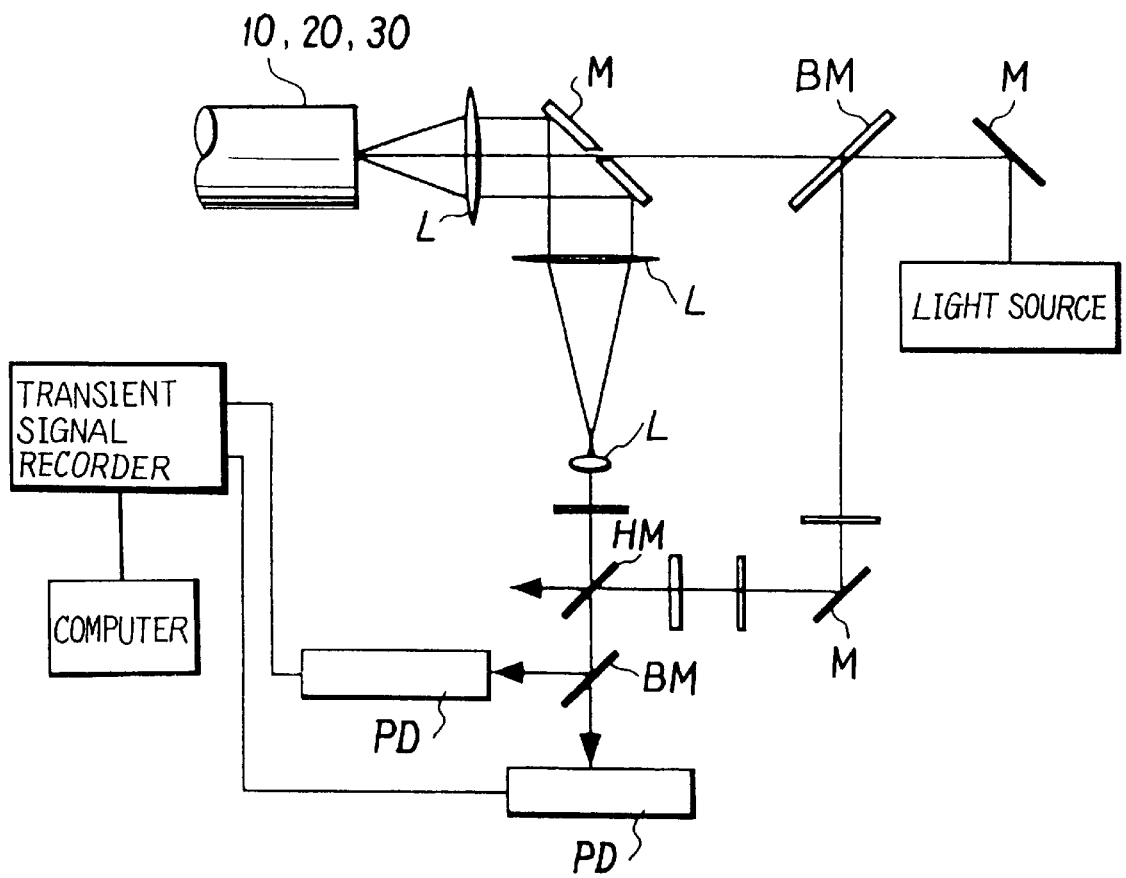
FIG. 7 is a block diagram of a laser interferometer employed in the first to third embodiments of the invention.

Shown in FIG. 7 is the general layout of the laser interferometer employed in the above-described first to third embodiments of the invention. In terms of operating principles, this interferometer is a Michelson interferometer for detection of Doppler shifts, and includes among its features independence of interference of P-polarized components from interference of S-polarized components, a phase difference of 90 between the P- and S-polarized components permitting detection of changes in direction of the velocity, and conversion and recording of all interference signals by a photodetector and a transient recorder instead of fringe counting, for analyzing sampled data after an experiment. The light source of the interferometer employs an argon laser.

In the drawings, denoted at L is a lens, at M a mirror, at PD a photodetector at HM a half mirror and at BM a beam splitter.

What is claimed is:

1. A method for testing frequency response characteristics of one of a laser displacement meter or a laser vibration meter, comprising the steps of:

applying impact on one end face of a round metal rod to produce an elastic wave pulse propagating toward the other end of said metal rod to generate stepwise dynamic displacement thereat by reflection of said elastic wave pulses;

measuring the stepwise dynamic displacement of the other end face of said metal rod simultaneously by a reference laser interferometer with a reference laser beam and said one of the laser displacement meter or the vibration meter with unknown frequency characteristics; and determining frequency response characteristics of said one of the laser displacement or the vibration meter by comparison of measurement data with counterpart data of said reference laser interferometer over a frequency range.

2. A method for testing frequency response characteristics of one of a laser displacement meter or a laser vibration meter, comprising the steps of:

applying an impulse voltage to a piezoelectric vibrator in a form of one of a piezoelectric element and a piezoelectric film to generate stepwise dynamic displacement on a surface of said piezoelectric vibrator;

measuring the stepwise dynamic displacement of said piezoelectric vibrator surface simultaneously by a reference laser interferometer with a reference laser beam and said one of the laser displacement meter or the laser vibration meter with unknown frequency response characteristics; and determining frequency response characteristics of said one of the laser displacement meter or the laser vibration meter by comparison of measurement data with counterpart measurement data of said reference laser interferometer over a frequency range.

3. A method for testing frequency response characteristics of one of a laser displacement meter or a vibration meter, comprising the steps of:

providing a piezoelectric film on an end face of a stack of piezoelectric elements;

applying an impulse voltage to said stack of piezoelectric elements to generate micro-level fine displacements on a surface of said piezoelectric film;

measuring said fine displacements of said piezoelectric film surface by the use of a reference laser interferometer with a reference laser beam to determine a phase correction value according to resulting measurement data;

measuring high-speed micro-level fine displacements of said piezoelectric film surface simultaneously by the use of said reference laser interferometer and said one of the laser displacement meter or a laser vibration meter with unknown frequency response characteristics; and determining frequency response characteristics of said said one of the laser displacement meter or the laser vibration meter by comparison of said resulting measurement data with the counterpart measurement data of said reference laser interferometer as corrected by said correction value.

* * * * *